United States Patent
Sweeney

(10) Patent No.: US 9,296,024 B2
(45) Date of Patent: Mar. 29, 2016

(54) MICROFIBER MEDICAL CLEANING DEVICE

(71) Applicant: Shaun Sweeney, Wayne, NJ (US)

(72) Inventor: Shaun Sweeney, Wayne, NJ (US)

(73) Assignee: CYGNUS MEDICAL, LLC, Branford, CT (US)

( * ) Notice: Subject to any disclaimer, the term of this patent is extended or adjusted under 35 U.S.C. 154(b) by 265 days.

(21) Appl. No.: 13/774,709

(22) Filed: Feb. 22, 2013

(65) Prior Publication Data

US 2014/0237748 A1 Aug. 28, 2014

(51) Int. Cl.
| | |
|---|---|
| *A61C 15/00* | (2006.01) |
| *B08B 9/043* | (2006.01) |
| *A61B 1/12* | (2006.01) |
| *A61B 19/00* | (2006.01) |
| *B08B 9/00* | (2006.01) |
| *B08B 1/00* | (2006.01) |

(52) U.S. Cl.
CPC .................. *B08B 9/043* (2013.01); *A61B 1/122* (2013.01); *A61B 19/34* (2013.01); *B08B 1/006* (2013.01); *B08B 9/00* (2013.01); *A61B 2019/343* (2013.01)

(58) Field of Classification Search
CPC .......... B08B 9/043; B08B 1/006; B08B 9/00; A61B 1/122; A61B 19/34; A61B 2019/343
See application file for complete search history.

(56) References Cited

U.S. PATENT DOCUMENTS

| | | | |
|---|---|---|---|
| 7,097,629 B2 * | 8/2006 | Blair | 604/1 |
| 2004/0187893 A1 | 9/2004 | Maguire, Jr. et al. | |
| 2006/0049386 A1* | 3/2006 | Kody et al. | 252/500 |
| 2006/0102200 A1 | 5/2006 | Esquenet et al. | |
| 2009/0113644 A1 | 5/2009 | Heck | |
| 2010/0229318 A1 | 9/2010 | Sparks | |
| 2011/0289705 A1 | 12/2011 | Asano et al. | |
| 2012/0324661 A1 | 12/2012 | DeDominicis et al. | |
| 2013/0269134 A1 | 10/2013 | Lin | |

OTHER PUBLICATIONS

European Search Report Application No. EP 14 15 6245 Completed: Apr. 4, 2014 6 pages.

* cited by examiner

*Primary Examiner* — Shay Karls
(74) *Attorney, Agent, or Firm* — St. Onge Steward Johnston & Reens LLC

(57) ABSTRACT

A medical cleaning device includes an introducer having a tail. A cleaning thread includes a microfiber strand bonded to a foam strand. The cleaning thread is folded to form a loop and woven to itself and the tail to form a scrubber. The introducer is configured to couple the cleaning device to a pulling device. The microfiber strand may be sonic welded to the foam strand. The woven cleaning thread may be sonic welded to itself and the tail at points along the scrubber. The foam strand may be composed at least partially of open-cell urethane foam. The pulling device may include a rod including a clip coupled to an introducer loop on the introducer.

18 Claims, 5 Drawing Sheets

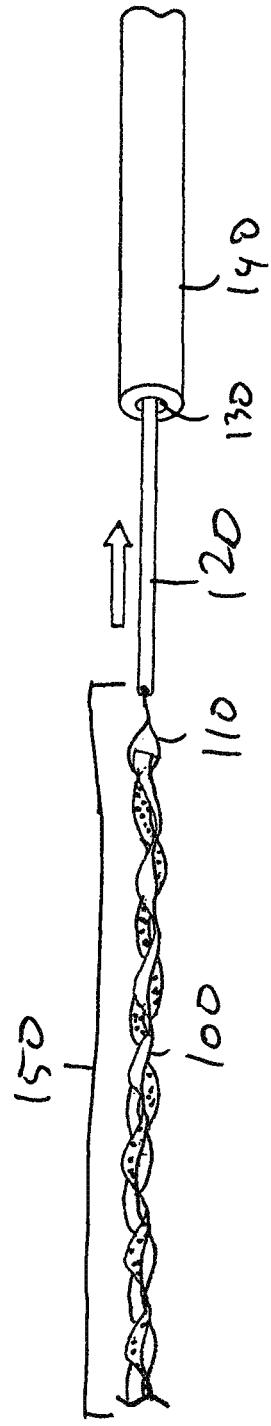
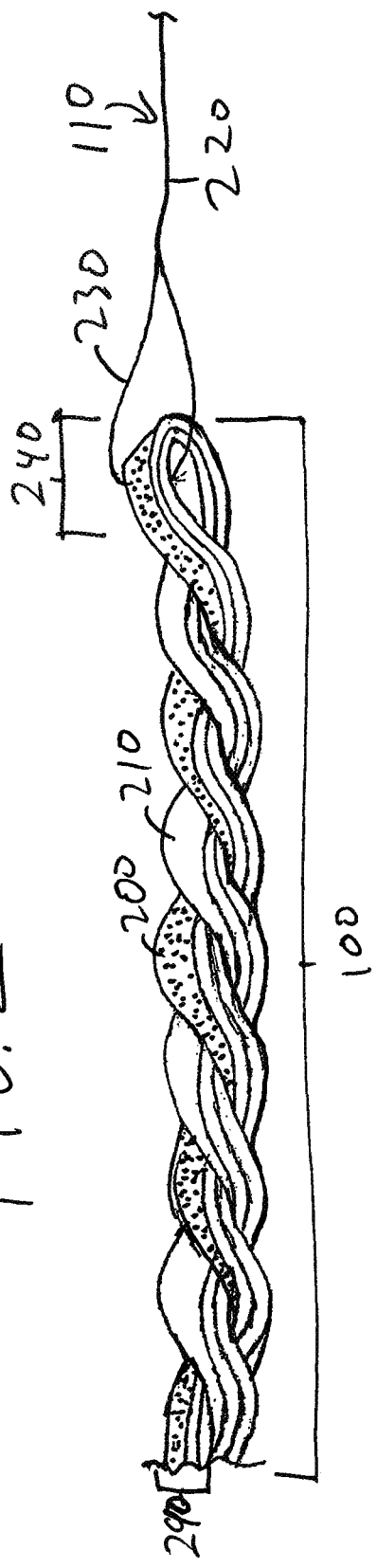

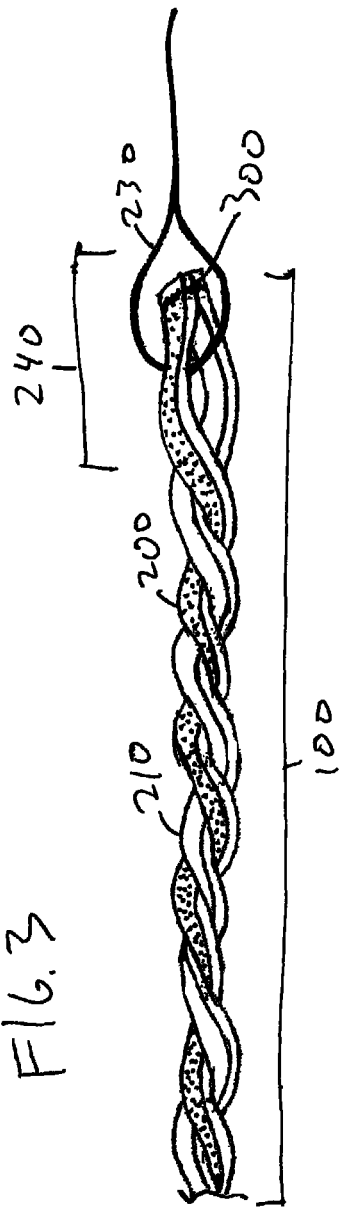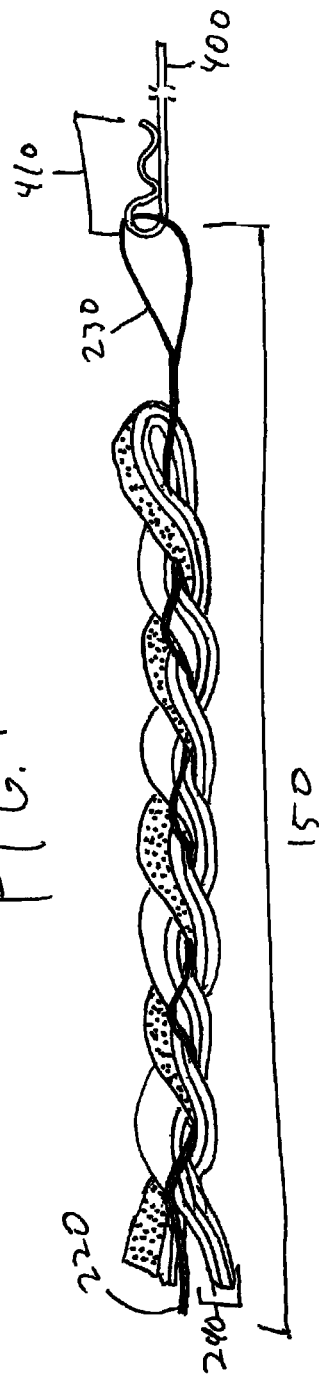

MICROFIBER MEDICAL CLEANING DEVICE

FIELD OF THE INVENTION

The present invention relates to an apparatus for cleaning. More specifically, the invention relates to a cleaning device for endoscopes and medical equipment.

BACKGROUND OF THE INVENTION

Surgery must be performed using clean and sterile instruments in order to prevent infection. Other medical devices also require cleaning and/or sterilization to maintain sanitary conditions in hospitals and other medical settings.

Surgical instruments must be cleaned and sterilized before every procedure, and each operation leaves biological residue on the instruments from the patient's body. This residue must be completely removed prior to sterilization. Some of these biological residues can be resilient and difficult to remove from the instruments. Thus, cleaning surgical instruments after a procedure requires specialized equipment and techniques.

The problem of bodily residue removal is further compounded by opportunistic organisms such as bacteria and fungi from the ambient environment and/or patient that colonize the instruments. These organisms produce a crude extracellular matrix in order to protect the cells in their colonies. This matrix is referred to as biofilm and usually comprises a disorganized web of long polymer strands interspersed with live cells and proteins. Biofilm is a highly effective anchoring and protection for bacterial and fungal colonies—as a result it is notoriously difficult to clean. Once a medical instrument is coated in biofilm, it is very difficult to fully clean and sterilize.

Currently several devices and solvents are used to clean instruments and remove biofilm. Although these systems are somewhat effective, they are not 100% effective and may require vigorous scrubbing and/or repeated cleaning. For example, surgical technicians usually use an inexpensive polyurethane foam material to wipe instruments. This foam will typically be soaked in detergent. Although the foam effectively delivers the detergent to the biofilm (resulting in a chemical degradation of the biofilm), the foam is not effective at mechanically abrading and removing the biofilm. This is because most common abrasive materials (including foam) do not have a microscopic structure capable of abrading biofilm.

Removing biofilm and biological residue from the exterior of medical instruments is challenging, but these difficulties are exacerbated in the context of endoscope or catheter lumen cleaning. Performing surgery using endoscopes is preferable to conventional open surgery because of lower patient mortality and morbidity. Endoscopy produces these more favorable outcomes because fewer unnecessary incisions are made to the patient in order to access the target tissue. However, cleaning and sterilizing endoscopes is difficult and necessary because endoscopes are expensive and must be reused to be economical.

During endoscopic surgery, the endoscope is inserted into the patient and oftentimes will have at least one lumen that evacuates fluids from the patient. This is done in order to remove unwanted materials such as resected tissue, cauterized tissue, blood, cellular contents, extra-cellular fluid, plasma, lymph, etc. . . . from the patient's body during the operation. This is done in order to improve visibility for the endoscopic camera and/or to reduce irritation/inflammation of surrounding tissues and reduce unwanted accumulation of fluid.

Once the endoscopic surgery is completed, not only is the endoscope's exterior coated with biological residue, but the interior of the lumens are as well. This residue must be completely removed from the endoscope before it can be reused for another procedure, since complete sterility is needed for any surgical instrument. Furthermore, the lumen interior is highly susceptible to hosting invasive organisms and accumulating biofilm.

The state of the art for cleaning and removing biofilm from lumen interiors is also essentially limited to detergent delivery systems (i.e. suctioning detergent through the lumen) and basic scrubbing devices. Many lumen cleaners use a "push through" design whereby a short scrubber is pushed through the lumen. A short scrubber must be used to prevent buckling as the scrubber moves through the channel. The Caterpillar™ endoscopic channel brush by Cygnus Medical, LLC is a pull-through design using a relatively rigid leader that is threaded through the channel. The leader is then used to pull a relatively long brush through the channel for improved cleaning. Although the Caterpillar™ represents a significant improvement, it employs a conventional scrubber brush and its ability to remove biofilm could be improved. Removing biofilm within lumens is a particularly demanding task, since the lumen interior is not physically accessible for vigorous scrubbing. Therefore, it is desirable to use the most abrasive material possible for cleaning the interiors of lumens.

One currently available highly abrasive material is melamine foam. Melamine foam only needs water to effectively remove most residues—no detergents or surfactants are required. Melamine foam has a unique microscopic structure that allows it to be both flexible and highly abrasive. When melamine resin cures into foam, its microstructure becomes very hard (almost as hard as glass), causing it to act like a very fine sandpaper. Melamine foam is flexible despite the base material's hardness because it is an open-celled foam, meaning that it is a sparse network of very hard strands. The open-cellular structure also aids in its cleaning ability because dirt particles are pulled into open cells and removed from the surface being cleaned. Despite these desirable qualities, melamine foam is not suitable for sterile cleaning applications because it crumbles as it scrubs. Leaving foam and debris particles on the instruments being cleaned is completely unacceptable for sterile applications as it virtually assures infection and contamination.

There remains a need in the art for a medical instrument cleaner that can simultaneously deliver detergent to biofilm while mechanically abrading, dislodging, and removing biofilm from the instrument without crumbling. It is particularly important to provide a device capable of fully removing biofilm from the interior of a catheter or endoscope lumen.

SUMMARY OF THE INVENTION

A medical cleaning pad includes a microfiber fabric layer and a scrubbing foam layer. The medical cleaning pad further includes a core foam layer sandwiched between and bonded to the microfiber fabric layer and scrubbing foam layer. In some embodiments, the core foam layer is at least twice as thick as the scrubbing foam layer. In some embodiments, the scrubbing foam layer is composed at least partially of open-cell urethane foam. In some embodiments, the core foam layer is composed at least partially of polyurethane foam. In some embodiments, the microfiber fabric layer is woven. In some embodiments, the microfiber fabric layer is non-woven.

In some embodiments, the scrubbing foam layer and microfiber fabric layer are flame laminated to the core foam layer.

A medical cleaning device includes a cleaning thread having a microfiber strand bonded to a foam strand. The cleaning thread is folded to form a scrubber loop and woven to itself to form a scrubber. The scrubber loop is configured to couple the cleaning device to a pulling device. In some embodiments, the microfiber strand is sonic welded to the foam strand. In some embodiments, the woven cleaning thread is sonic welded to itself at points along the scrubber. In some embodiments, the foam strand is composed at least partially of open-cell urethane foam. In some embodiments, the pulling device includes an introducer having an introducer loop coupled to the scrubber loop and a rod coupled to a tail of the introducer.

A medical cleaning device includes a microfiber strand and a foam strand. An end of the foam strand is coupled to an end of the microfiber strand to form a scrubber loop configured to couple the cleaning device to a pulling device. The foam strand and microfiber strand are woven to each other to form a scrubber. In some embodiments, the end of the microfiber strand is sonic welded to the end of the foam strand. In some embodiments, the foam strand and the microfiber strand are sonic welded to each other at points along the scrubber. In some embodiments, the foam strand is composed at least partially of open-cell urethane foam. In some embodiments, the pulling device includes an introducer having an introducer loop coupled to the scrubber loop and a rod coupled to a tail of the introducer.

A medical cleaning device includes an introducer having a tail. A cleaning thread includes a microfiber strand bonded to a foam strand. The cleaning thread is woven to itself and the tail to form a scrubber. The introducer is configured to couple the cleaning device to a pulling device. In some embodiments, the microfiber strand is sonic welded to the foam strand. In some embodiments, the woven cleaning thread is sonic welded to itself and the tail at points along the scrubber. In some embodiments, the foam strand may be composed at least partially of open-cell urethane foam. In some embodiments, the pulling device includes a rod including a clip coupled to an introducer loop on the introducer.

A medical cleaning device includes a scrubbing foam article that removes biofilm particles from a biofilm adhered to a surface being cleaned. The medical cleaning device also includes a microfiber article that collects the particles and removes them from the vicinity of the surface being cleaned.

A medical cleaning device includes a microfiber strand. The medical cleaning device also includes a foam strand coupled to the microfiber strand. The foam strand and microfiber strand are woven to form a scrubber.

BRIEF DESCRIPTION OF THE DRAWINGS

FIG. 1 is an isometric view of a medical cleaning device being pulled into an endoscopic lumen.

FIG. 2 is a close-up isometric view of a medical cleaning device coupled to an introducer.

FIG. 3 is an isometric view of a medical cleaning device coupled to an introducer.

FIG. 4 is an isometric view of a medical cleaning device woven with an introducer and coupled to a puller.

DETAILED DESCRIPTION OF THE INVENTION

Figure 5:
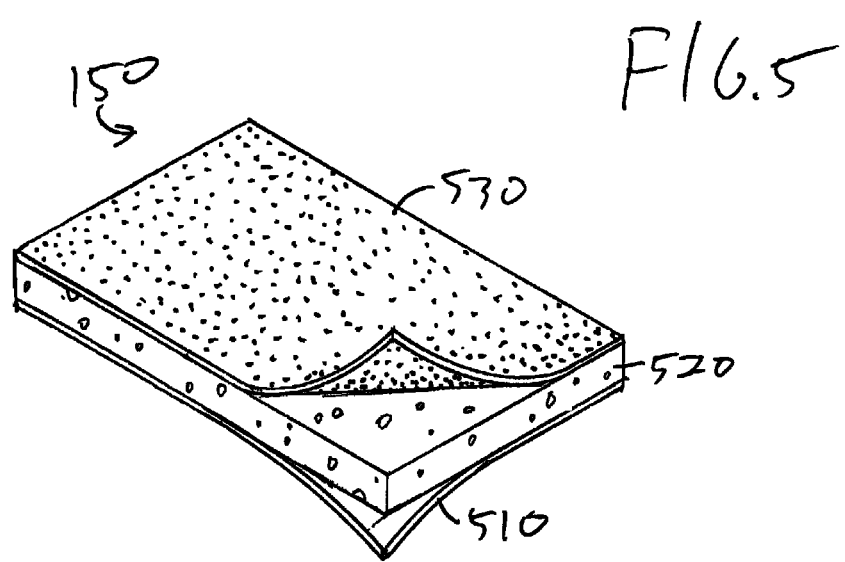
FIG. 5 is an isometric view of a medical cleaning device with the layers peeled back.

FIG. 1 is an isometric view of a medical cleaning device 150 according to one embodiment being pulled into a lumen 130 of an endoscope 140. Medical cleaning device 150 comprises a scrubber 100, an introducer 110, and a rod 120. Rod 120 is bonded to introducer 110 by an adhesive or sonic welding. Scrubber 100 is pulled through lumen 130 using rod 120. Generally, scrubber 100 will have a diameter approximately 20% larger than lumen 130 to ensure snug fit between scrubber 100 and lumen 130 as scrubber 100 is pulled through.

FIG. 2 is a close-up of the introducer 110 and scrubber 100. Scrubber 100 comprises a cleaning thread 290 comprising a microfiber strand 210 bonded to a foam strand 200. Microfiber strand 210 is bonded to foam strand 200 by sonic welding in this embodiment, but may be bonded by an adhesive, thermal bond, or another type of bond. Cleaning thread 290 is folded to form a scrubber loop 240 and woven to itself to form scrubber 100. Scrubber loop 240 is coupled to introducer loop 230 on introducer 110. This is accomplished by threading cleaning thread 290 through introducer loop 230 and subsequently weaving cleaning thread 290 to form scrubber 100. In another embodiment, introducer 100 is threaded through scrubber loop 240 and bonded to itself to form introducer loop 230. Cleaning thread 290 is sonic welded in spots along the weave in some embodiments to prevent unwinding of scrubber 100. In some embodiments, scrubber 100 is about six inches long once woven.

In some embodiments, introducer 110 is off-the-shelf dental floss introducer or a specially fabricated part. Introducer 110 comprises introducer loop 230 and tail 220. In some embodiments, introducer 110 can be fabricated by thermally bonding or sonically welding a thread to itself. Tail 220 of introducer 110 is sonically welded, thermally bonded, adhered, or otherwise affixed to rod 120. In some embodiments, rod 120 is a hollow tube whereby tail 220 is inserted into the tube and bonded to the interior of the tube. In some embodiments, rod 120 is a disposable plastic tube.

Foam strand 200 comprises special foam that is capable of abrading biofilm. In some embodiments, foam strand 200 comprises a rigid, abrasive foam such as microporous open-cell foam. In some embodiments, foam strand 200 is a open-cell urethane foam. In some embodiments, foam strand comprises a matrix of polymers having a very high material hardness. These properties allow foam strand 200 to operate like an extremely fine sandpaper which interacts with the tiny grooves and pits on the instrument surfaces being cleaned. These properties allow it to completely remove biofilm. Foam strand 200 abrades biofilm as scrubber 100 is pulled through lumen 130. This process loosens debris and generally removes biofilm from the interior surface of lumen 130. Furthermore, dislodged particles are pulled into the open cells of foam strand 200.

Figure 7:
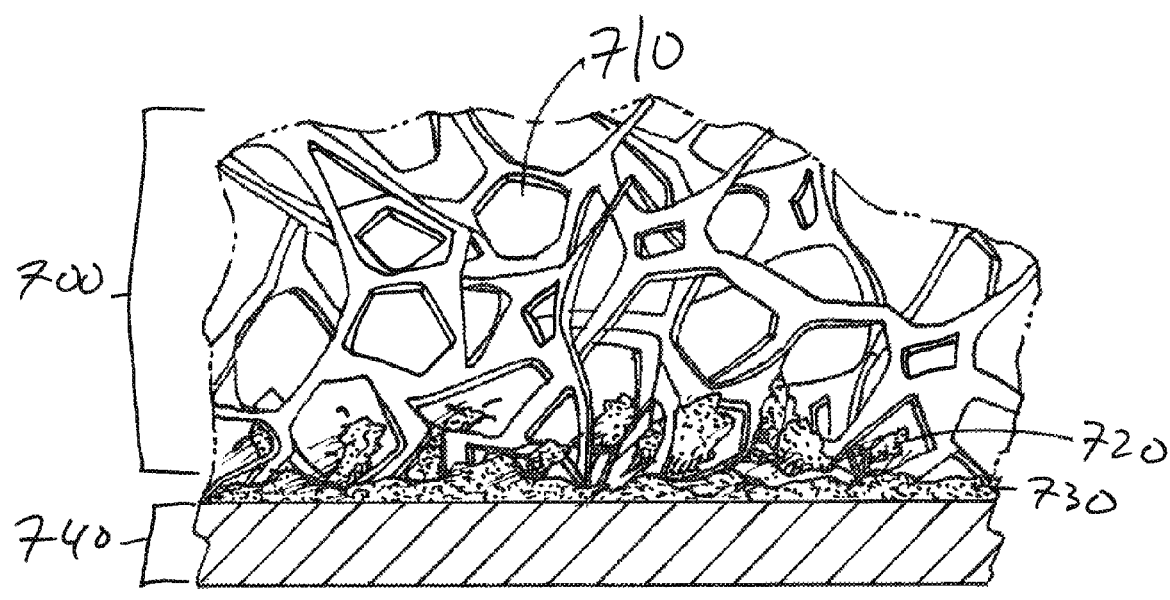
FIG. 7 is a microscopic view of open-cell foam scrubbing an instrument surface and removing biofilm.

FIG. 7 shows a microscopic view of the structure of open-cell foam as described above. Open-cell foam 700 comprises a network of interconnected rigid polymers forming open cells 710. This allows foam 700 to remove particles 720 of biofilm 730 adhered to a instrument surface 740 as shown in FIG. 7. Particles 720 are also pulled into the open cells 710, which aids in their removal. Open-cell foam 700 is an urethane foam in some embodiments. An open-cell urethane foam 700 as described herein is suitable for sterile cleaning applications because it does not crumble like melamine foam.

It is similar to melamine foam in its microscopic structure and rigidity; however, it is less brittle and prone to crumbling.

Microfiber strand 210 comprises microfiber fabric that has a microscopic structure allowing it to accumulate and retain fine particles. Once debris has been detached from the interior surface of lumen 130 by foam strand 200, microfiber strand 210 captures and sweeps up the debris. Microfiber strand 210 is capable of capturing microscopic particles as small as four microns. This debris is removed from lumen 130 with scrubber 100 once scrubber 100 has been fully pulled through lumen 130. Scrubber 100 may be soaked in detergent or surfactant to aid this process by further chemically degrading the biofilm. In that case, foam strand 200 and/or microfiber strand 210 retains the detergent and delivers it to the interior surface of lumen 130.

Figure 8:
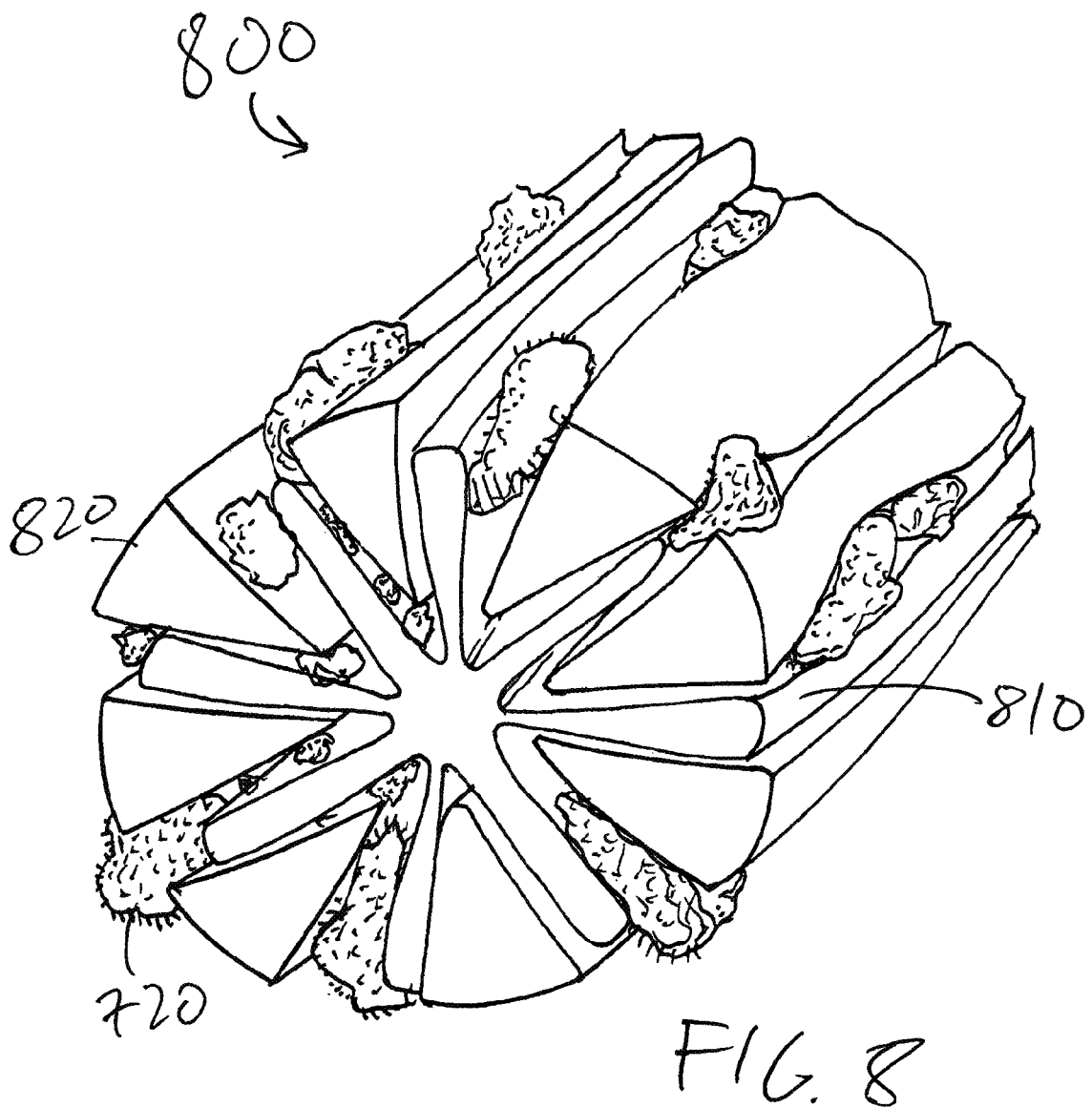
FIG. 8 is a microscopic view of microfiber accumulating particles of biofilm.

FIG. 8 shows a microscopic view of a single fiber 800 used to create a microfiber fabric. The microfiber comprises a star component 810 and several wedge components 820. When microfiber 800 contacts biofilm particles 720, particles 720 become trapped between star component 810 and one of the wedge components 820. If sufficient microfiber fabric is used, substantially all of the particles dislodged by the scrubbing foam can be swept up by the microfiber fabric and completely removed from the medical instrument surface when the cleaning device is removed.

FIG. 3 is an isometric view of a medical cleaning device according to the embodiment shown in FIG. 1 coupled to an introducer. In this embodiment, microfiber strand 210 and foam strand 200 are woven to each other and bonded at one end. In this embodiment, the two strands are bonded by sonic weld 300. The strands are bonded to form scrubber loop 240, which is coupled to introducer loop 230. Foam strand 200 and microfiber strand 210 are bonded by thermal bonding, adhesive, or other bonds in other embodiments. Introducer tail 220 can then be coupled to a rod 120 and threaded into a lumen 130.

FIG. 4 is an isometric view of a medical cleaning device 150 according to the embodiment shown in FIG. 1 woven with introducer 110 and coupled to a puller 400. Tail 220 of introducer about the same length as scrubber 100 (or about half the length of cleaning thread 290) and is woven with cleaning thread 290 to create scrubber 100. The woven cleaning thread 290 and tail 220 are sonic welded at points to prevent the woven scrubber 100 from unwinding. In other embodiments, cleaning thread 290 and tail 220 are bonded by thermal bonding, adhesive, or other bonds to prevent unwinding of woven scrubber 100. In the embodiment shown in FIG. 4, introducer loop 230 protrudes from the end of scrubber 100 in the vicinity of scrubber loop 240.

Introducer loop 230 is attached to rod 400 which comprises a clip 410 at one end that resembles a bobby-pin. Once introducer loop 230 and rod 400 are coupled, rod 400 can be threaded through lumen 130 and used to subsequently pull introducer 110 and scrubber 100 through lumen 130. In some embodiments rod 400 as shown in FIG. 4 is an approximately twelve inch long steel rod and reusable for multiple lumen 130 cleanings.

Figure 6:
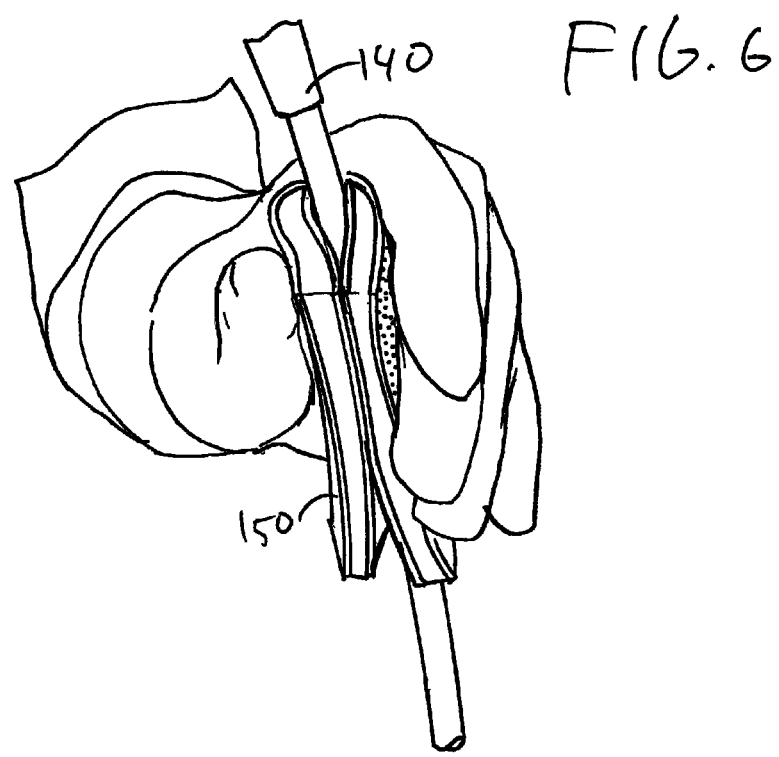
FIG. 6 is a medical cleaning device being used to wipe the outside of an endoscope.

FIG. 5 is an isometric view of a medical cleaning device 150 according to one embodiment with the layers peeled back. Medical cleaning device 150 in this embodiment is a pad comprising three layers. The layers include a scrubbing foam layer 530, a core foam layer 520, and a microfiber layer 510. The medical cleaning device 150 of FIG. 5 may be constructed by flame laminating the scrubbing foam layer 530 and microfiber layer 510 to core foam layer 520. FIG. 6 shows the medical cleaning device 150 from FIG. 5 being used to clean the exterior surface of an endoscope 140.

Scrubbing foam layer 530 is a rigid, abrasive foam such as microporous open-cell foam. In some embodiments, scrubbing foam layer 530 is a open cell urethane foam. In some embodiments, scrubbing foam layer 530 comprises a matrix of polymers having a very high material hardness. These properties allow it to operate like an extremely fine sandpaper which interacts with the tiny grooves and pits of the instrument surfaces being cleaned. Furthermore, these properties allow scrubbing foam layer 530 to completely remove biofilm from surfaces it is adhered to. Furthermore, dislodged particles are pulled into the open cells of foam strand 200.

Due to the materials used to form scrubbing foam layer 530 in this embodiment, it has some structural drawbacks for use in a large pad for cleaning medical instruments. Specifically, a thick layer of this type of foam is too rigid to wrap around or conform to the shape of instruments as shown in FIG. 6. Thus, a thin scrubbing foam layer 530 is used adhered to a thicker core foam layer 520 made of a more flexible and resilient foam such as polyurethane foam. This provides structural and cleaning properties required for cleaning medical instruments, and allows the medical cleaning device 150 to bend and contour around the instruments.

A pad without a flexible core foam layer 520 (and/or with a thicker scrubbing foam layer 530) is suitable for cleaning sturdy, flat objects, and may be present in other embodiments. In those embodiments, scrubbing foam layer 530 is bonded directly to microfiber layer 510. In some embodiments, scrubbing foam layer is flame laminated to microfiber layer 510. In some embodiments the scrubbing foam layer 530 is thicker than the microfiber layer 510, for example, three times as thick or more.

Medical cleaning device 150 as shown in FIGS. 5 and 6 also comprises microfiber fabric layer 510. Microfiber layer 510 may be a woven or non-woven fabric depending on application. For example, a non-woven fabric may be used for non-sterile applications and a more expensive woven fabric may be used for sterile applications since less fibers will be released and deposited on instruments during cleaning. As discussed with regard to the lumen scrubber 100, the microfiber is capable of capturing free-floating particles of biofilm or bio residue. Microfiber layer 510 is capable of capturing microscopic particles as small as four microns. Thus, this layer can be used to wipe clean a surface that has previously been scrubbed using detergent and scrubbing foam layer 530.

Medical cleaning device 150 may be soaked in detergent or surfactant to aid this process by further chemically degrading the biofilm. In that case, scrubbing foam layer 530, core foam layer 520, and/or microfiber layer 510 retains the detergent and delivers it to the instrument surfaces being cleaned. In some embodiments, medical cleaning device 150 is used "dry" without any solvent, or is only soaked in distilled water.

Although the invention has been described with reference to embodiments herein, those embodiments do not limit the scope of the invention. Modifications to those embodiments or different embodiments may fall within the scope of the invention.

What is claimed is:

1. A medical cleaning device, comprising:
   a cleaning thread comprising a microfiber strand bonded to a foam strand;
   said cleaning thread being folded to form a scrubber loop and woven to itself to form a scrubber;
   the scrubber loop being configured to couple the cleaning device to a pulling device.

2. The medical cleaning device of claim 1, wherein the microfiber strand is sonic welded to the foam strand.

3. The medical cleaning device of claim 1, wherein said woven cleaning thread is sonic welded to itself at points along the scrubber.

4. The medical cleaning device of claim 1, wherein the foam strand comprises open-cell urethane foam.

5. The medical cleaning device of claim 1, wherein the pulling device comprises:
   an introducer comprising an introducer loop coupled to the scrubber loop; and
   a rod coupled to a tail of the introducer.

6. A cleaning device, comprising:
   a microfiber strand;
   a foam strand;
   an end of said foam strand being coupled to an end of said microfiber strand to form a scrubber loop configured to couple the cleaning device to a pulling device;
   said foam strand and microfiber strand being woven to each other to form a scrubber.

7. The cleaning device of claim 6, wherein the end of said microfiber strand is sonic welded to the end of said foam strand.

8. The cleaning device of claim 6, wherein said foam strand and said microfiber strand are sonic welded to each other at points along the scrubber.

9. The cleaning device of claim 6, wherein said foam strand comprises open-cell urethane foam.

10. The cleaning device of claim 6, wherein the pulling device comprises:
    an introducer comprising an introducer loop coupled to the scrubber loop; and
    a rod coupled to a tail of the introducer.

11. A cleaning device, comprising:
    a microfiber strand;
    a foam strand;
    said foam strand and microfiber strand being bonded or woven together to form a cleaning thread;
    the cleaning thread including a loop formed by folding the cleaning thread or by coupling an end of said foam strand to an end of said microfiber strand;
    wherein the loop is configured to couple the cleaning thread to a pulling device.

12. The cleaning device of claim 11, wherein said microfiber strand is bonded to said foam strand to form the cleaning thread; wherein the cleaning thread is folded to form the loop.

13. The medical cleaning device of claim 11, wherein said foam strand and microfiber strand are woven to each other to form the cleaning thread; wherein the end of said foam strand is coupled to the end of said microfiber strand to form the loop.

14. The cleaning device according to claim 11, wherein said scrubbing foam strand removes biofilm particles from a biofilm adhered to a surface being cleaned and said microfiber strand collects the particles and removes them from the vicinity of the surface being cleaned.

15. A medical cleaning device, comprising:
    a cleaning thread comprising a plurality of strands, the strands being connected to one another to form a scrubber, at least one of the strands comprising microfiber fabric;
    a pulling device; and
    the scrubber being folded at a proximal end to couple the cleaning device to said pulling device.

16. The medical cleaning device according to claim 15, wherein:
    said pulling device includes an introducer and a rod, the introducer including a first end coupled to the folded proximal end of the scrubber and a second end having a tail;
    wherein the tail of the introducer is inserted within the rod.

17. The medical cleaning device of claim 15, wherein the tail of the introducer is bonded to an interior portion of the rod.

18. The medical cleaning device of claim 15, wherein at least one of the strands is a foam strand.

* * * * *